United States Patent [19]

Ahluwalia et al.

[11] Patent Number: 5,364,885
[45] Date of Patent: Nov. 15, 1994

[54] REDUCTION OF HAIR GROWTH

[76] Inventors: Gurpreet S. Ahluwalia, 8632 Stable View Ct., Gaithersburg, Md. 20879; Douglas Shander, 16112 Howard Landing Dr., Gaithersburg, Md. 20878

[21] Appl. No.: 976,446

[22] Filed: Nov. 13, 1992

[51] Int. Cl.$^5$ .................... A61K 31/195; A61K 31/16
[52] U.S. Cl. ...................................... 514/563; 514/629
[58] Field of Search ................................. 514/563, 629

[56] References Cited

U.S. PATENT DOCUMENTS

| | | | |
|---|---|---|---|
| 3,092,548 | 6/1963 | Worton | 514/563 |
| 3,285,818 | 11/1966 | Ohta et al. | 167/87 |
| 3,426,137 | 2/1969 | Philpitt et al. | 424/65 |
| 3,600,279 | 8/1971 | Takahashi et al. | 435/280 |
| 3,808,196 | 4/1974 | Yoshinzumi et al. | 536/17.9 |
| 3,996,246 | 12/1976 | Hoffman | 549/319 |
| 4,039,669 | 8/1977 | Beyler et al. | 514/178 |
| 4,045,450 | 8/1977 | Kinugasa | 549/319 |
| 4,139,638 | 2/1979 | Neri et al. | 514/624 |
| 4,161,540 | 7/1979 | Neri et al. | 514/624 |
| 4,167,522 | 2/1980 | Gilonnier et al. | 424/304 |
| 4,191,775 | 3/1980 | Glen | 424/304 |
| 4,269,831 | 5/1981 | Ferrari et al. | 424/241 |
| 4,344,941 | 8/1982 | Wiechert et al. | 424/243 |
| 4,370,315 | 1/1983 | Greff et al. | 424/94 |
| 4,439,432 | 3/1984 | Peat | 424/240 |
| 4,720,489 | 1/1988 | Shander | 514/171 |
| 4,885,289 | 12/1989 | Brener et al. | 514/170 |
| 5,095,007 | 3/1992 | Ahluwalia | 514/23 |
| 5,096,911 | 3/1992 | Ahluwalia et al. | 514/23 |
| 5,132,293 | 7/1992 | Shander et al. | 514/46 |
| 5,143,925 | 9/1992 | Shander et al. | 514/378 |

FOREIGN PATENT DOCUMENTS

| | | |
|---|---|---|
| 1208132 | 7/1986 | Canada . |
| 244387 | 6/1988 | Czechoslovakia . |
| 3501 | 10/1965 | France . |
| 41651 | 10/1964 | Germany . |
| 3439486 | 1/1986 | Germany . |
| 48034818 | 9/1971 | Japan . |
| 48085526 | 2/1972 | Japan . |
| 48085527 | 2/1972 | Japan . |
| 48085528 | 2/1972 | Japan . |
| 48085529 | 2/1972 | Japan . |
| 7862820 | 6/1978 | Japan . |
| 55129277 | 3/1979 | Japan . |
| 8407113 | 1/1984 | Japan . |
| 61210021 | 3/1985 | Japan . |
| 61289016 | 6/1985 | Japan . |
| 86210021 | 9/1986 | Japan . |
| 86289016 | 12/1986 | Japan . |
| 63243017 | 3/1987 | Japan . |
| 1034282 | 7/1987 | Japan . |
| 88243017 | 7/1988 | Japan . |
| 65009008 | 4/1989 | Japan . |
| 417633 | 4/1981 | Switzerland . |
| 657967 | 10/1986 | Switzerland . |
| 844439 | 7/1971 | United Kingdom . |
| 879259 | 3/1972 | United Kingdom . |
| 1033843 | 11/1974 | United Kingdom . |
| 1145623 | 4/1975 | United Kingdom . |
| 1458349 | 12/1976 | United Kingdom . |
| 87-046603/07 | 3/1987 | WIPO . |
| WO91/14431 | 10/1991 | WIPO . |

OTHER PUBLICATIONS

*Gould Medical Dictionary*, 0301, Ed., McGraw-Hill Book Co. 3rd edition, p. 81 (1972).

(List continued on next page.)

*Primary Examiner*—Marianne M. Cintins
*Assistant Examiner*—K. Weddington
*Attorney, Agent, or Firm*—Fish & Richardson

[57] ABSTRACT

Mammalian hair growth is reduced by applying to the skin a composition including pantothenic acid or an analogue of pantothenic acid.

23 Claims, No Drawings

OTHER PUBLICATIONS

Burdick et al., "The Topical Effect of the Antiandrogen Chlormadinone Acetate and Some of Its Chemical Modifications on the Hamster Costovertebral Organ," Br. J. Derm., vol. 82, Suppl. 6, p. 19 (1970).

Fidanza, "Therapeutic Action of Pantothenic Acid", pp. 53–67 (1977).

Girard et al., "Inhibition of Testosterone Metabolism and Lipogenesis in Animal Sebaceous Glands by Progesterone", Arch. dermatol. Res., 269:281–290 (1980).

Goos et al., "An Improved Method for Evaluating Antiandrogens", Arch. Dermatol. Res., 273:333–342 (1982).

"Final Report on the Safety Assessment of Panthenol and Pantothenic Acid", J. Am. Coll. Toxic., 8:139–162 (1987).

Matthews et al., "Vitamins—Part III–Water-Soluble", NPhA Journal, pp. 6–12 (1982).

Simpson et al., "The effect of topically applied progesterone on sebum excretion rate", Brit. Journ. of Derm., 100:687–692 (1979).

REDUCTION OF HAIR GROWTH

This invention relates to inhibition of mammalian hair growth.

U.S. Pat. No. 4,039,669 describes the topical use of 17-alpha-R-androst-4-en-17-beta-ol-3-one or esters thereof where the R is n-propyl or n-butyl for the control of dermatological systems associated with androgen-mediated conditions such as acne.

U.S. Pat. Nos. 4,139,638 and 4,161,540 describe the use of certain 4'-substituted and 3',4'-disubstituted anilides for the treatment of androgen-dependent disease states such as female hirsutism and acne.

U.S. Pat. No. 4,191,775 discloses that certain 3,4-disubstituted branched-chain fluorinated acylanilides may be used in the topical treatment of androgen-dependent disease conditions such as acne, female hirsutism, and seborrhea.

U.S. Pat. No. 4,344,941, describes the topical use of certain androgenic 17-alpha-substituted steroids exemplified by 17-beta-hydroxyl-1-alpha-methyl-17-alpha(1-methyl-2-propenyl)-5-alpha-androstan-3-one for the treatment of diseases such as acne, seborrhea, alopecia and female hirsutism.

West German OLS 2,840,144 describes the use of a combination of progesterone with either cyproterone acetate or chlormadinone acetate in the topical treatment of androgen induced hormonal disturbances such as alopecia, female hirsutism, and acne.

The patent art discloses a number of ways of reducing the growth of human hair as opposed to its conventional removal by cutting, shaving, or depilation. One such method is described in U.S. Pat. No. 3,426,137, which pertains to a process for inhibiting the growth of hair by the topical application to a depilated skin area of a composition containing a substituted benzophenone such as 2-amino-5-chloro-benzophenone. Examples in the patent illustrate the reduction of hair growth on the back area of rabbits and on the arm of a male human subject.

Another process for extending the duration of depilation is described in U.S. Pat. No. 4,370,315. The process therein comprises the topical application of a composition containing a lipoxygenase along with linoleic acid or derivative thereof. The patent describes the application of such composition to various body parts of female human subjects in the majority of which regrowth of hair was clearly perceptible only after six or more weeks.

In U.S. Pat. No. 4,439,432 topical compositions containing progesterone are reported for use in treatment of progesterone deficiency and related conditions, including abnormal hair growth resulting from androgen excess. Further insights on this point may be obtained from the related literature, among which mention may be made of Simpson et al. "The Effect of Topically Applied Progesterone on Sebum Excretion Rate," Br. J. Derm., Vol. 100, p. 687 (1979), in which progesterone was reported effective in reducing sebum excretion rates in females, but without effect in males. In Goos et al., "An Improved Method for Evaluating Antiandrogens," Arch. Dermatol. Res. vol. 273, pp. 333–341 (1982), the effect of progesterone on inhibition of hair growth in intact males appears to be doubtful (p. 340, Table 3, Group VI vs. Group X). In Burdick et al., "The Topical Effect of the Antiandrogen Chlormadinone Acetate and Some of Its Chemical Modifications on the Hamster Costovertebral Organ," Br. J. Derm,. Vol 82, Supplement 6, p. 19 (1970), antiandrogens were either ineffective or of questionable effect in inhibiting flank organ function in normal intact male hamsters. Similarly, in Girard et al., "Inhibition of Testosterone Metabolism and Lipogenesis in Animal Sebaceous Glands by Progesterone," Arch. Dermatol. Res., Vol. 269, pp. 281–290 (1980), progesterone is found effective in the female but not in the male. In all of the above experiments topical antiandrogens were ineffective in males in inhibiting androgenic function. When the female and male responses were compared in both humans and hamsters, only females responded to topical treatment.

In U.S. Pat. No. 4,269,831 a substantial reduction in hair growth of the hamster flank organ is among the effects reported from topical application of $17\beta$-hydroxy-$17\alpha$-propylandrost-4-en-3-one. However reduction in the size of the flank organ is also described, leaving a smaller field on which the hair can grow. Therefore, the reduction in hair growth may be a consequence of a decrease in area of the flank organ rather than an alteration in the character of the hair.

U.S. Pat. No. 4,885,289 describes altering the rate and character hair growth by topical application of 5-alpha-reductase inhibitors and/or cytoplasmic androgen receptor binding agents, while U.S. Pat. No. 4,720,489 describes the topical application of ornithine decarboxylase inhibitors for similar purposes, either alone or in combination with the materials of U.S. Pat. No. 4,885,289. U.S. Pat. No. 5,095,007 describes inhibiting hair growth by applying inhibitors of adenylosuccinate synthetase or aspartate transcarbanylase. U.S. Pat. No. 5,096,911 describes inhibiting mammalian hair growth by applying inhibitors of gamma-glutamyl transpeptidase. U.S. Pat. No. 5,132,293 describes inhibiting mammalian hair growth by applying inhibitors of 5-adenosylmethionine decarboxylase.

Pantothenic acid has been previously used in hair treatment methods. However, previous methods have focused on the use of pantothenic acid as a hair moisturizer and stimulant of scalp hair growth. See, e.g., J. Am. College Toxicology 139 (1987) and Japanese Patent Publication No. 2,430,170.

It has now been found that mammalian (including human) hair growth can be inhibited by applying to the skin a composition including pantothenic acid, or an analog of pantothenic acid, in an amount effective to reduce hair growth in the applied area.

Pantothenic acid includes a carboxylic acid group that can be in either free (—COOH) or salt (—COOX, where X is a counterion) form. Accordingly, "pantothenic acid", as used herein, is meant to encompass both free and salt forms.

Analogs of pantothenic acid include derivatives, conjugates, and homologs of pantothenic acid, and salts thereof. Examples of derivatives of pantothenic acid include pantothenyl alcohol, calcium 4-phosphonpantothenate, and 4'-amino-4'deoxypanthothenic acid; examples of conjugates of pantothenic acid include D-pantethine (a conjugate of pantothenic acid and cysteamine), pantetheine-S-sulfonate, 4-phospho-S-benzoylpantetheine; and examples of homologs of pantothenic acid include hopantenate [calcium 4-(2,4-dihydroxy-3,3-dimethylbutyramido)butyrate hemihydrate].

The composition preferably includes a non-toxic dermatologically acceptable vehicle or carrier which is adapted to be spread upon the skin. Examples of suitable vehicles are: a hydroalcoholic vehicle, cream, lotion or gel which can effectively deliver the active compound to site of application. In addition, a penetration enchancer(s) may be added to the vehicle to further enhance the effectiveness of the formulation.

The concentration of the inhibitor in the composition may be varied over a wide range up to a saturated solution, preferably from 1 to 30% by weight or even more; the reduction of hair growth increases as the amount of inhibitor applied increases per unit area of skin. The maximum amount effectively applied is limited only by the rate at which the inhibitor penetrates the skin. Generally, the effective amounts range from 100 to 3000 micrograms or more per square centimeter of skin.

The composition should be applied to the area of the body where it is desired to inhibit hair growth. Typically, the composition can be applied to the face, particularly to the beard area of the face such as the cheek and chin. The composition can also be applied to the legs, arms, torso or armpit. In humans, the composition should be applied twice a day, or even more frequently, for at least three months to achieve a perceived reduction in hair growth.

Reduction of hair growth is demonstrated when the frequency of hair removal is reduced, or the subject perceives less hair on the treated site, or, quantitatively, when the weight of hair removed by shaving (i.e., hair mass) is reduced.

The following specific examples are intended to illustrate more clearly the nature of the present invention without acting as a limitation upon its scope.

EXAMPLE 1

A vehicle or carrier was prepared having the following composition:

| Component | Wt. Percent Concentration |
|---|---|
| Distilled Water | 68% |
| Ethanol (100 proof) | 16% |
| Propylene glycol | 5% |
| Dipropylene glycol | 5% |
| Benzyl alcohol | 4% |
| Propylene carbonate | 2% |

Pantothenic acid hemicalcium salt (PTA) was mixed with separate portions of the foregoing vehicle to provide specimens containing 5, 10, 20, and 30% by weight, respectively, the pH of these formulations was in the range of pH 7–8.

A group of male intact Golden Syrian hamsters was provided. These animals were considered acceptable models for human beard hair growth in that they display oval shaped flank organs, one on each side, each about 8 mm. in major diameter, which grow thick black and coarse hair similar to human beard hair. These organs produce hair in response to androgens in the hamster. The flank organs of each hamster were depilated by applying a thioglycolate based chemical depilatory (Surgex), and to one organ of each animal was applied 10-25 μl. of vehicle alone once a day, while to the other organ of each animal was applied an equal amount of vehicle containing the analog. After thirteen applications (one application per day for five days a week), the flank organs were shaved and the amount of recovered hair (hair mass) from each was weighed. Percent-reduction of hair growth was calculated by subtracting the hair mass (mg) value of the test compound treated side from the hair mass value of the vehicle treated side; the delta value obtained was then divided by the hair mass value of the vehicle treated side, and the resultant number was multiplied by 100. The results were as shown in Table 1.

EXAMPLE 2

D-Pantothenic acid monosodium salt (PTAss) was mixed with separate portions of the vehicle of Example 1 to provide specimens containing 5, 10, 20, and 30% by weight, respectively, of the analog and the pH of these formulations was in the range of pH 7–8.

A group of male intact Golden Syrian hamsters was treated as in Example 1, and percent inhibition was determined. The results were as shown in Table 1.

EXAMPLE 3

Pantoyl alcohol (PTYA) was mixed with separate portions of the vehicle of Example 1 to provide specimens containing 5, 10, 20, and 30% by weight, respectively, of the analog and the pH was in the range of pH 7–8.

Two groups of male intact Golden Syrian hamsters were treated as in Example 1, and percent inhibition was determined. The results were as shown in Table 1.

EXAMPLE 4

As a comparison to a known inhibitor of hair growth, described in U.S. Pat. No. 4,720,480 one group of eight animals was treated with a composition containing 10% DFMO ($\alpha$-difluoromethyl ornithine) in the vehicle of Example 1; the pH of this formulation was 4.0. The treatments were as described in Example 1. The results were as shown in Table 1.

EXAMPLE 5

As a control, one group of eight animals had both flank organs of each animal treated with vehicle alone. The results were as shown in Table 1.

TABLE 1

Inhibition of Hair Growth By Pantothenic Acid Analogs
Hamster Flank Organ Hair Mass
(mg ± SEM)

| Treatments | (n) | Treated | Untreated | % Inhibition (+ SEM) |
|---|---|---|---|---|
| 5% PTA | 8 | .738 ± .13 | 2.281 ± .23 | 67.35 ± 5.81 |
| 10% PTA | 7 | .424 ± .11 | 1.716 ± .23 | 71.27 ± 8.96 |
| 20% PTA | 7 | .270 ± .12 | 1.777 ± .23 | 85.85 ± 5.75 |
| 30% PTA | 8 | .160 ± .06 | 2.326 ± .25 | 92.74 ± 2.76 |
| 5% PTAss | 8 | .644 ± .15 | 2.345 ± .23 | 72.57 ± 5.18 |
| 10% PTAss | 7 | .364 ± .10 | 1.713 ± .20 | 80.11 ± 4.38 |
| 20% PTAss | 7 | .500 ± .10 | 1.944 ± .10 | 74.17 ± 4.83 |
| 30% PTAss | 8 | .396 ± .95 | 1.868 ± .28 | 79.78 ± 4.75 |
| 5% D-PTYA | 7 | 1.069 ± .15 | 2.416 ± .23 | 55.87 ± 4.32 |
| 10% D-PTYA | 8 | 1.095 ± .32 | 2.120 ± .20 | 48.27 ± 10.96 |
| 20% D-PTYA | 8 | .899 ± .30 | 1.481 ± .32 | 31.38 ± 13.84 |
| 30% D-PTYA | 8 | 1.069 ± .26 | 1.625 ± .30 | 34.75 ± 8.49 |
| 5% DL-PTYA | 8 | 2.670 ± .23 | 2.516 ± .24 | <−8.28 ± 7.51> |
| 10% DL-PTYA | 7 | 1.490 ± .30 | 2.463 ± .28 | 40.30 ± 7.35 |
| 20% DL-PTYA | 8 | 1.450 ± .21 | 3.075 ± .21 | 51.14 ± 7.49 |
| 30% DL-PTYA | 8 | .708 ± .13 | 2.567 ± .19 | 70.83 ± 5.95 |
| 10% DFMO | 8 | .631 ± .12 | 2.115 ± .37 | 66.10 ± 7.05 |

TABLE 1-continued

Inhibition of Hair Growth By Pantothenic Acid Analogs
Hamster Flank Organ Hair Mass
(mg ± SEM)

| Treatments | (n) | Treated | Untreated | % Inhibition (+ SEM) |
|---|---|---|---|---|
| Control | 8 | 1.938 ± .16 | 2.191 ± .18 | 9.72 ± 6.46 |

PTA: D-Pantothenic acid hemicalcium salt
PTAss: D-Pantothenic acid monosodium salt
PTYA: D-, or DL-, Pantothenyl alcohol It will be appreciated by those skilled in the art that the invention can be performed within a wide range of equivalent parameters of composition and conditions without departing from the spirit or scope of the invention or of any embodiment thereof.

We claim:

1. A process of reducing mammalian hair growth, comprising
   selecting an area of mammalian skin from which a reduced rate of hair growth is desired; and
   applying a composition comprising pantothenic acid or an analog of pantothenic acid in an amount effective to reduce hair growth to said area of mammalian skin to cause a reduction in the rate of hair growth from said area of mammalian skin.

2. The process as claimed in claim 1, wherein said composition includes pantothenic acid.

3. The process as claimed in claim 1, wherein the concentration of said pantothenic acid or said analog of pantothenic acid in the composition is from 1 to 30%.

4. The process as claimed in claim 1, wherein the composition is applied to the skin in an amount of from 100 to 3000 micrograms of said pantothenic acid or said analog of pantothenic acid per square centimeter of skin.

5. The process as claimed in claim 1, wherein the composition is applied to skin on the face or neck of said mammal.

6. The process as claimed in claim 1, wherein the composition is applied to the skin on a leg of said mammal.

7. The process as claimed in claim 1, wherein the composition is applied to the skin on the arm of said mammal.

8. The process as claimed in claim 1, wherein the composition is applied to the skin on the torso of said mammal.

9. The process as claimed in claim 1, wherein the composition is applied to skin on the armpit of said mammal.

10. The process of claim 1, wherein said composition includes pantothenyl alcohol.

11. The process of claim 1, wherein said composition includes calcium 4-phosphopantothenate.

12. The process of claim 1, wherein said composition includes 4'-amino-4'-desoxypanthothenic acid.

13. The process of claim 1, wherein said composition includes D-pantethine.

14. The process of claim 1, wherein said composition includes pantethine-S-sulfonate.

15. The process of claim 1, wherein said composition includes 4-phospho-S-benzoylpantethine.

16. The process of claim 1, wherein said composition includes hopantenate.

17. The process of claim 1, wherein said composition includes a derivative of pantothenic acid.

18. The process of claim 1, wherein said composition includes a conjugate of pantothenic acid.

19. The process of claim 1, wherein said composition includes a homolog of pantothenic acid.

20. The process of claim 1, wherein said mammalian skin is human skin and said area of human skin to which said composition is applied is an area of skin comprising beard hair.

21. The process of claim 1, wherein said hair growth that is reduced is androgen-stimulated hair growth.

22. The process of claim 1, wherein said composition, when tested in the Golden Syrian hamster assay, provides a reduction in hair growth of at least about 40.3%.

23. The process of claim 1, wherein said composition, when tested in the Golden Syrian hamster assay, provides a reduction in hair growth of at least about 51.14%.

* * * * *

UNITED STATES PATENT AND TRADEMARK OFFICE
CERTIFICATE OF CORRECTION

PATENT NO. : 5,364,885

DATED : November 15, 1994

INVENTOR(S) : Gurpreet S. Ahluwalia et al.

It is certified that error appears in the above-identified patent and that said Letters Patent is hereby corrected as shown below:

In column 5, claim 1, line 22, "comprising" should be --including--.

Signed and Sealed this

Sixteenth Day of January, 1996

Attest:

BRUCE LEHMAN

Attesting Officer

Commissioner of Patents and Trademarks